US006600075B1

(12) United States Patent
Whittle et al.

(10) Patent No.: US 6,600,075 B1
(45) Date of Patent: Jul. 29, 2003

(54) PROCESS FOR THE PREPARATION OF TERTIARY AMINES FROM PRIMARY AMINES AND NITRILES

(75) Inventors: Kelley Moran Whittle, Wilmington, DE (US); Alan Martin Allgeier, Wilmington, DE (US); Thomas Papin Gannett, Wilmington, DE (US); David Page Higley, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/053,073

(22) Filed: Nov. 13, 2001

(51) Int. Cl.$^7$ .................... C07C 209/48; C07C 255/04
(52) U.S. Cl. .................. 564/490; 564/491; 564/492; 564/506; 564/507; 558/451; 558/454; 558/455
(58) Field of Search ................... 564/490, 491, 564/492, 506, 507; 558/451, 454, 455

(56) References Cited

U.S. PATENT DOCUMENTS

| | | | |
|---|---|---|---|
| 3,673,251 A | | 6/1972 | Frampton |
| 4,093,657 A | * | 6/1978 | Schoenewaldt et al. |
| 4,650,671 A | * | 3/1987 | Golman ................ 424/66 |
| 5,086,136 A | * | 2/1992 | Takashima et al. ......... 526/177 |
| 5,463,130 A | | 10/1995 | Witzel et al. |
| 5,557,011 A | | 9/1996 | Witzel et al. |
| 5,648,545 A | | 7/1997 | Reif et al. |
| 5,894,074 A | | 4/1999 | Fuchs et al. |
| 6,198,002 B1 | * | 3/2001 | Eller et al. .................. 564/491 |
| 6,248,925 B1 | * | 6/2001 | Ford et al. .................. 564/470 |
| 6,331,624 B1 | * | 12/2001 | Koch et al. .................. 540/538 |
| 6,399,830 B1 | * | 6/2002 | Armor et al. ................ 564/490 |

OTHER PUBLICATIONS

Vasileva, E. I.; Freidlina, R. KH. Institute of Heteroorganic Compounds, Academy of Sciences of the USSR; Translated from Ivestiya Akademi Nauk SSSR, Seriya Khimicheskaya, No. 2, pp. 237–240, Feb., 1966; Original Article Submitted Aug. 21, 1963.

* cited by examiner

Primary Examiner—Shailendra Kumar

(57) ABSTRACT

Disclosed is a method for preparing tertiary amine compounds from primary amines and nitrites in the presence of hydrogen gas and a metal catalyst, or metal-containing catalyst composition, at a temperature from about 50° C. to about 200° C. and at a pressure from about 100 psig to 1500 psig. The primary amines and the nitriles used in the process may be diamines and/or dinitriles, or may be combinations of primary amines and/or nitrites. Also disclosed are novel tertiary amine compounds made by the described method.

18 Claims, No Drawings

PROCESS FOR THE PREPARATION OF TERTIARY AMINES FROM PRIMARY AMINES AND NITRILES

FIELD OF INVENTION

The present invention relates to a method for the preparation of tertiary amines from primary amines and nitrile moieties under reductive conditions, and products made by such method.

BACKGROUND OF THE INVENTION

New techniques for efficiently preparing common or novel chemicals are continuously sought after by the chemical industry. In particular, any improvements in the synthesis of tertiary amines would be highly valuable, as there are many applications. These applications include use as bioactives, buffers, precursors for surfactants, corrosion inhibitors, and polyurethane catalysts. The ability to incorporate additional functionality, such as nitriles, alcohols, ethers, amides, additional tertiary amine centers, aryl groups, and fluorinated alkyl groups would also be desirable. The additional functionality would allow for the incorporation of a highly functionalized substrate into a polymer backbone, affording the polymer unique properties.

It is known in the art that under reductive conditions nitriles react with amines to form alkylated amine products. For example, excess dimethylamine, when reacted with adiponitrile under catalytic reductive conditions, undergoes a single reductive amination onto each nitrile to give N,N,N',N'-tetramethylhexamethylenediamine (U.S. Pat. No. 5,463,130, U.S. Pat. No. 5,557,011 and U.S. Pat. No. 5,894,074). In addition to tertiary amine formation from the reaction of a secondary amine with a nitrile, U.S. Pat. No. 3,673,251 discloses the formation of secondary amines by the reaction of primary amines with a nitrile. For example, 1,1'-di-(N-methylaminomethyl)biphenyl-3,3' can be obtained from the reaction of methylamine and 1,1'-dicyanobiphenyl-3,3'. However, there has been no disclosure of a method for preparing a tertiary amine directly from a primary amine and a nitrile.

There is also need for a method that will efficiently provide bis(cyanoalkyl)aminoalkanes, as these compounds are useful precursors for natural products, for substrates that exhibit antitumor activity, and for polymer dye-site additives. To date, these targets have been synthesized by multi-step processes that require the use of an expensive halo-alkylnitrile as an intermediate. For example, Russian researchers (Vasil'eva, E. I.; Freidlina, R. Kh. Izvestiya Akademii Nauk S S R, Seriya Khimicheskaya, No.2, pp. 237–240, February, 1966) disclose the synthesis of bis(5-cyanobutyl)aminomethane, where methylamine reacts with two equivalents of chlorovaleronitrile.

Since there has been no disclosure of the preparation of tertiary amines directly from primary amines and nitrites, tertiary amines that would be useful in similar applications are unavailable because there are no commercially viable routes to these compounds. A novel route to known tertiary amines and novel tertiary amines prepared from primary amines and nitrites is needed to increase the availability of these types of compounds.

SUMMARY OF THE INVENTION

Disclosed herein is a method for preparing at least one tertiary amine product having the formula

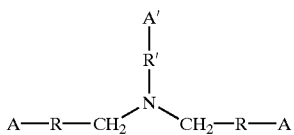

(I)

wherein R and R' independently are C1–C12 substituents selected from the group consisting of straight or branched aliphatic, cycloaliphatic, and heterocyclic moieties; and wherein A is selected from the group consisting of hydrogen, cyano, amide, straight or branched aliphatic, cycloaliphatic, aromatic, heterocyclic, alkoxy, aryloxy, hydroxy, alkylamino, dialkylamino, arylamino, diarylamino, haloaryl, fluorinated alkyl, and silyl moieties;

wherein A' is selected from the group consisting of hydrogen, amino, amide, straight or branched aliphatic, cycloaliphatic, aromatic, heterocyclic, alkoxy, aryloxy, hydroxy, alkylamino, dialkylamino, arylamino, diarylamino, haloaryl, fluorinated alkyl, and silyl;

said method comprising contacting a primary amine having the general formula $$H_2N-R'-A' \qquad (III)$$

wherein R' is a C1–C12 substituent selected from the group consisting of straight or branched aliphatic, cycloaliphatic, and heterocyclic moieties;

wherein A' is selected from the group consisting of hydrogen, amino, amide, straight or branched aliphatic, cycloaliphatic, aromatic, heterocyclic, alkoxy, aryloxy, hydroxy, alkylamino, dialkylamino, arylamino, diarylamino, haloaryl, fluorinated alkyl, and silyl moieties;

with at least one nitrile having the general formula $$A-R-CN \qquad (II)$$

wherein R is a C1–C12 substituent selected from the group consisting of straight or branched aliphatic, cycloaliphatic, and heterocyclic moieties;

wherein A is selected from the group consisting of hydrogen, cyano, amide, straight or branched aliphatic, cycloaliphatic, aromatic, heterocyclic, alkoxy, aryloxy, hydroxy, alkylamino, dialkylamino, arylamino, diarylamino, haloaryl, fluorinated alkyl, and silyl moieties;

in the presence of hydrogen gas and a catalyst at a temperature from about 50° C. to about 200° C. and at a pressure from about 100 psig to 1500 psig.

Also disclosed are tertiary amine compounds prepared by the method described above.

A further disclosure of the present invention are novel tertiary amine compounds having the formulae:

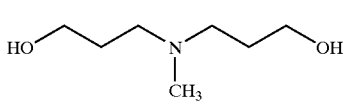

(V)

-continued

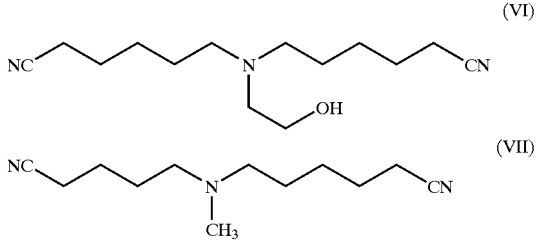

(VI)

(VII)

DETAILED DESCRIPTION OF THE INVENTION

The present invention discloses a method for preparing tertiary amines from a primary amine and a nitrile moiety under reductive conditions. The method is carried out by contacting at least one nitrile compound with at least one primary amine compound. It is preferred that the nitrile is used in molar excess of the primary amine. The method can be described generally by equation A.

(A)

wherein R and R' independently are C1–C12 straight or branched aliphatic, cycloaliphatic, or heterocyclic; and wherein A is selected from the group consisting of hydrogen, cyano, amide, straight or branched aliphatic, cycloaliphatic, aromatic, heterocyclic, alkoxy, aryloxy, hydroxy, alkylamino, dialkylamino, arylamino, diarylamino, haloaryl, fluorinated alkyl, and silyl;

wherein A' is selected from the group consisting of hydrogen, amino, amide, straight or branched aliphatic, cycloaliphatic, aromatic, heterocyclic, alkoxy, aryloxy, hydroxy, alkylamino, dialkylamino, arylamino, diarylamino, haloaryl, fluorinated alkyl, and silyl.

A few of the many types of compounds that can be prepared by this process include simple trialkyl amines, where one can vary the identity of the alkyl chains around the nitrogen center, making, in the simplest of cases, diethylmethylamine from acetonitrile and methylamine. A diamine, such as 1,3-diaminopropane, can also be reacted in the same manner with acetronitrile to obtain N,N,N',N'-tetraethyl-1,3-propanediamine. Diols with an internal tertiary amine can be formed by reacting cyano-alkanols with primary amines, under the conditions described herein. Another class of compounds afforded efficiently by this invention is bis(cyanoalkyl)aminoalkanes, which are formed by the reaction of dinitriles with primary amines. By varying the functionality on the primary amine and subsequent hydrogenation of the resulting nitriles, one can produce unique monomers that have a tertiary amine and two primary amines. These unique monomers can then be incorporated into polymers to give the polymers unique physical properties.

Some of the suitable starting nitrites that can be used in the method of the present invention are depicted in structure (II) below. These compounds can be mono- or bi- or multi-functional. That is, they may contain one or more nitrile groups, and may have one or more other functional groups. The R group is a C1 to C12 straight or branched aliphatic, cycloaliphatic, or heterocyclic moiety. The A group is hydrogen, cyano, amide, straight or branched aliphatic, cycloaliphatic, aromatic, heterocyclic, alkoxy, aryloxy, hydroxy, alkylamino, dialkylamino, arylamino, diarylamino, haloaryl, fluorinated alkyl, or silyl moiety.

$$A—R—CN \quad (II)$$

Suitable starting amines for the present invention can be monoprimary amines or diprimary amines of the structure (III) below, where R' is a C1–C12 straight or branched aliphatic, cycloaliphatic, or heterocyclic moiety; and where A' is hydrogen, amino, amide, straight or branched aliphatic, cycloaliphatic, aromatic, heterocyclic, alkoxy, aryloxy, hydroxy, alkylamino, dialkylamino, arylamino, diarylamino, haloaryl, fluorinated alkyl, or a silyl moiety.

$$A'—R'—NH_2 \quad (III)$$

The present invention can be carded out using a 1:1 molar ratio of nitrile to amine. Preferred is an excess of the nitrile to the amine, from about 2:1 to about 5:1. Most preferred is a nitrile to amine ratio of about 2:1 to about 4:1.

Primary amines that may be used in the present invention can be diamines (having two amine groups, for example, 1,2-diaminocyclohexane). Similarly, the nitrile of the present invention may be a dinitrile (having two nitrile groups, for example, adiponitrile). Also, the combinations of starting amines and starting nitrites may be varied. For example, either a monoamine or a diamine may be used in the method of the present invention with either a mononitrile or a dinitrile. Additionally, one or more primary amines may be used with a combination of nitrites; or one or more nitrites with a combination of amines. The use of a combination of nitriles is exemplified in Table 1 below, but is not intended to limit the scope of the invention described herein.

Suitable catalysts for the present invention comprise the metal elements selected from the group consisting of palladium, rhodium, platinum, and iridium. Preferred catalysts are catalysts comprising palladium. Examples of catalysts comprising palladium include, but are not limited to, palladium black or palladium on a support, wherein the palladium content on the support is between about 0.1 and 10 wt. % loading. The catalyst also can be comprised of mixed metal compositions. For example the catalyst may comprise palladium with between about 0.1 and 10% of at least one additional metal. The preferred elements for the mixed metal compositions to be used with palladium are selected from the group consisting of rhodium, platinum, iridium and ruthenium.

Other catalyst systems, such as copper oxide-zirconium oxide, which are known to promote single reductive amination reactions can be used also.

A support material can be used with the catayst of the present invention. Suitable supports include, but are not limited to, activated carbon, silicon carbide and oxidic supports, (for example, alumina, silica, titania, zirconia, magnesia, copper oxide).

The catalyst can be used in any desired form, including but not limited to extrudate, large granules, pellet, sphere, slurry or dry powder.

The method of the present invention is carried out under hydrogen pressure of between about 100 and about 1500 psig. Hydrogen pressures between about 500 and 1000 psig are most preferred. The temperature should be maintained between about 50° C. and about 200° C., with about 80° C. to about 130° C. being preferred.

Solvents are not necessary to carry out the method. However solvents such as water, methanol, ethanol, tertiary-butyl ether, tetrahydrofuran, and N-methylpyrrolidinone and other solvents known to dissolve the starting amine and nitrile compounds are suitable. Also, the present invention may be carried out batchwise or in a continuous reactor. The final alkylated amine product can be purified in a conventional manner.

EXAMPLES

The following examples were carried out in batch mode.
Legend:
BCPAM means bis(5-cyanopentyl)aminomethane
ADN means adiponitrile Example 1

Using 4:1 Molar Ratio of Nitrile and Primary Amine to Prepare bis(5-Cyanopentyl)aminomethane (Shown Below as Structure (VIII)) (IUPAC Name: 6-[(5-Cyano-pentyl)-methyl-amino]hexanenitrile)

To a 300 cc pressure autoclave reactor were charged 2.77 g of 5% Pd/alumina powder catalyst(2.3% or 42:1 nitrile to catalyst), 20.8 g of 40% (w/w) aqueous methylamine (0.27 mol), and 116.0 g of ADN (1.1 mol). The reactor was sealed and purged with nitrogen and hydrogen to remove oxygen. The reaction was conducted at 110° C. under 500 psig of hydrogen. The consumed hydrogen was constantly replenished from a 1-liter vessel. After 120 min the reaction mixture comprised 47% ADN, 41% BCPAM and other products. The selectivity to BCPAM was 79%.

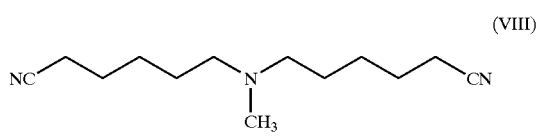

(VIII)

Example 2

Using 2:1 Molar Ratio of Nitrile and Primary Amine to Prepare bis(5-Cyanopentyl)aminomethane (IUPAC name: 6-[(5-Cyano-pentyl)-methyl-amino]-hexanenitrile)

To a 300 cc pressure autoclave reactor were charged 5.46 g of 5% Pd/alumina powder catalyst, 41.6 g of 40% (w/w) aqueous methylamine (0.54 mol), and 116.0 g of ADN (1.1 mol). The reactor was sealed and purged with nitrogen and hydrogen to remove oxygen. The reaction was conducted at 110° C. under 500 psig of hydrogen. The consumed hydrogen was constantly replenished from a 1-liter vessel. After 575 min the reaction mixture comprised 6% ADN, 67% BCPAM and other products. The selectivity to BCPAM was 72%.

Example 3

Preparation of bis(5-Cyanopentyl)aminopropane 116.0 g of adiponitrile and 15.7 mL of propylamine, (4 to 1 ratio of dinitrile to primary amine) were charged to a 300 cc autoclave along with 2.8 grams of catalyst (5 wt. % Pd on alumina powder). After purging with nitrogen, the reaction was pressurized to 50 psig with hydrogen and heating was commenced. Hydrogen was continuously replenished. After the temperature reached 110° C., stirring was increased to 1000 rpm and the hydrogen pressure was increased to 500 psig. The temperature and pressure were maintained for 1.5 hours. The product mixture comprised of 39% bis (cyanopentyl)aminopropane and 36% unconverted adiponitrile.

Examples 4–8 in Table 1 demonstrate the disclosed method using different or a combination of nitriles with various amines. The examples were carried out in batch mode, using 1 part 5 wt. % Pd/Al$_2$O$_3$ catalyst to 20 parts of starting nitrile; and a hydrogen pressure of 500 psig and a temperature of 100° C. were maintained for 3 hours. The unique tertiary amine products of Examples 4, 6 and 8 were analyzed by IR using a Perkin Elmer 1600 Series Fourier Transform Infrared Instrument and a Hewlett Packard 5971 Series Mass Selective Detector in conjunction with a Hewlett Packard 5890 Series Gas Chromatograph.

Analyses demonstrate the preparation of unique tertiary amines having the following structures:

| Example | Structure |
|---|---|
| 4 | HO~~~N(CH$_3$)~~~OH (V) |
| 6 | NC~~~~~N(~~OH)~~~~~CN (VI) |
| 8 | NC~~~~N(CH$_3$)~~~~~CN (VII) |

TABLE 1

| Ex. No./ Nitrile to Amine Molar Ratio | Conv | Starting Nitrile | Starting Amine | Tertiary Amine Product IUPAC name | Tertiary Amine Yield |
|---|---|---|---|---|---|
| 4 2 to 1 | 86% | Hydroxy Propio-nitrile | Methyl-amine | bis(3-hydroxypropyl) aminomethane | 31% |
| 5 4 to 1 | >99% | Aceto-nitrile | Propane-diamine | N,N,N',N'-tetraethyl-1,3-propanediamine | 74% |
| 6 2 to 1 | 82% | Adipo-nitrile | 2-amino-ethanol | 3-bis(cyanopentyl) amino-ethanol | 51% |
| 7 4 to 1 | >99% | Aceto-nitrile | 1,2-diamino-cyclo-hexane | N,N,N'-triethyl-1,2-diaminocyclo-hexane | 40% |
| 8 2 to 1 | 95% | 1:1 mixture of adipo-nitrile and glutaro-nitrile | Methyl-amine | mixture of tertiary amines, including cyanobutyl-cyanopentylamino-methane | 58% |

The examples in Table 2 demonstrate the use of different catalysts in the disclosed method. The following examples were carried out in batch mode, using 1 part catalyst to 20 parts of adiponitrile. The molar ratio of methylamine (40 wt. % aq.) to adiponitrile was 1 to 4 in each case. Hydrogen pressure of 500 psig and temperature of 100° C. were maintained for 3 hours.

TABLE 2

| Ex. | Catalyst Used | Conversions | Tertiary Amine Yield |
|-----|---------------|-------------|----------------------|
| 9   | 5% Pd/Carbon  | >99%        | 71%                  |
| 10  | 4% Pd/ 1% Pt on Carbon | >99% | 58%             |
| 11  | 4.5% Pd/ 0.5% Ru on Carbon | >99% | 63%        |
| 12  | 5% Pd/Titania | >99%        | 75%                  |
| 13  | 5% Pt/Carbon  | 86%         | 19%                  |
| 14  | 5% Rh/Carbon  | >99%        | 6%                   |

Example 15

Using 1:1 Molar Ratio of Nitrile to Primary Amine

To a 300 cc pressure autoclave reactor were charged 3.66 g of 5% Pd/alumina powder catalyst, 55.8 g of 40% (w/w) aqueous methylamine (0.72 mol), 77.7 g of adiponitrile (0.72 mol) and 2.3 g biphenyl (internal standard for gas chromatography analysis). The reactor was sealed and purged with nitrogen and hydrogen to remove oxygen. The reaction was conducted at 110° C. under 500 psig of hydrogen. The consumed hydrogen was constantly replenished from a 1-liter vessel. After 240 min an analysis of the crude product mixture comprised 13% adiponitrile, 46% BCPAM. The selectivity was 65%.

After 300 min the crude product mixture comprised 4% adiponitrile, 52% BCPAM, and other products. The selectivity to BCPAM was 62%.

Example 16

1:2 Molar Ratio of Adiponitrile to Primary Amine

To a 300 cc pressure autoclave reactor were charged 2.74 g of 5% Pd/alumina powder catalyst, 83.71 g of 40% (w/w) aqueous methylamine (1.1 mol), 58.3 g of adiponitrile (0.54 mol) and 1.7 g biphenyl (internal standard for gas chromatography analysis). The reactor was sealed and purged with nitrogen and hydrogen to remove oxygen. The reaction was conducted at 110° C. under 500 psig of hydrogen. The consumed hydrogen was constantly replenished from a 1-liter vessel. After 360 min the reaction mixture comprised 12% ADN, 29% BCPAM. The selectivity was 49%. After 410 min the reaction mixture comprised 5% ADN, 31% BCPAM. The selectivity was 44%.

What is claimed is:

1. A method for preparing at least one tertiary amine product having the formula $$\begin{array}{c} A' \\ | \\ R' \\ | \\ A-R-CH_2-N-CH_2-R-A \end{array} \quad (I)$$

wherein R is a C1–C12 substituent selected from the group consisting of straight or branched aliphatic, cycloaliphatic, and heterocyclic moieties;

wherein R' is a C1–C12 substituent selected from the group consisting of straight or branched aliphatic, cycloaliphatic, and heterocyclic moieties;

wherein A is selected from the group consisting of hydrogen, cyano, amide, straight or branched aliphatic, cycloaliphatic, aromatic, heterocyclic, alkoxy, aryloxy, hydroxy, alkylamino, dialkylamino, arylamino, diarylamino, haloaryl, fluorinated alkyl, and silyl;

wherein A' is selected from the group consisting of hydrogen, amino, amide, straight or branched aliphatic, cycloaliphatic, aromatic, heterocyclic, alkoxy, aryloxy, hydroxy, alkylamino, dialkylamino, arylamino, diarylamino, haloaryl, fluorinated alkyl, and silyl;

said method comprising contacting at least one primary amine having the general formula $$H_2N-R'-A' \quad (III)$$

wherein R' is a C1–C12 substituent selected from the group consisting of straight or branched aliphatic, cycloaliphatic, or heterocyclic moieties; and wherein A' is selected from the group consisting of hydrogen, amino, amide, straight or branched aliphatic, cycloaliphatic, aromatic, heterocyclic, alkoxy, aryloxy, hydroxy, alkylamino, dialkylamino, arylamino, diarylamino, haloaryl, fluorinated alkyl, and silyl moieties;

with at least one nitrile having the general formula $$A-R-CN \quad (II)$$

wherein R is a C1–C12 substituent selected from the group consisting of straight or branched aliphatic, cycloaliphatic, and heterocyclic moieties; and wherein A is selected from the group consisting of hydrogen, cyano, amide, straight or branched aliphatic, cycloaliphatic, aromatic, heterocyclic, alkoxy, aryloxy, hydroxy, alkylamino, dialkylamino, arylamino, diarylamino, haloaryl, fluorinated alkyl, and silyl moieties;

with the proviso that when A is either H or straight or branched aliphatic, and R is straight or branched aliphatic, said nitrile is a C2–C7 nitrile;

in the presence of hydrogen gas and a catalyst at a temperature from about 50° C. to about 200° C. and at a pressure from about 100 psig to about 1500 psig, and wherein the ratio of nitrile to amine is greater than 1:1.

2. The method of claim 1 wherein the catalyst comprises at least one metal element selected from the group consisting of palladium, iridium, rhodium, and platinum.

3. The method of claim 2 wherein the catalyst comprises palladium.

4. The method of claim 2 wherein said catalyst comprises at least two metals.

5. The method of claim 2 wherein the catalyst is supported on alumina, silica, titania, zirconia, silicon carbide, activated carbon, copper oxide or magnesium oxide.

6. The method of claim 5 wherein the catalyst is present in an amount of about 0.1 weight percent to about 10 weight percent of the support.

7. The method of claim 1 wherein more than one nitrile compound is contacted with at least one amine.

8. The method of claim 1 wherein more than one amine is contacted with at least one nitrile.

9. The method of claim 1 wherein a tertiary amine product is $$\begin{array}{c} \text{VIII} \\ NC\diagup\diagdown\diagup\diagdown\diagup N \diagdown\diagup\diagdown\diagup\diagdown CN \\ | \\ CH_3 \end{array}$$

10. A compound prepared by the method of claim 1.

11. A compound according to claim 10 wherein the amine is methylamine and the nitrile is adiponitrile.

12. A compound according to claim 10 wherein the amine is methylamine and the nitrile is hydroxypropionitrile.

13. A compound according to claim 10 wherein the nitrile is adiponitrile, and wherein said amine is 2-aminoethanol.

14. A compound according to claim 10 wherein said amine is methylamine, and wherein said nitrile is a mixture of a 1:1 molar ratio of adiponitrile and glutaronitrile.

15. A tertiary amine product having the structure (VI)

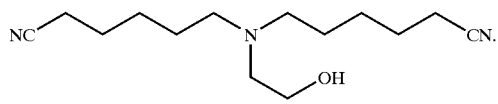

(VI)

16. A tertiary amine product having the structure (VII)

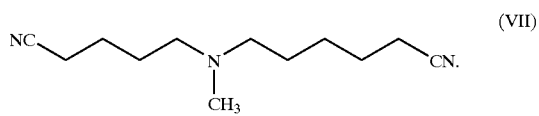

(VII)

17. A compound having the formula:

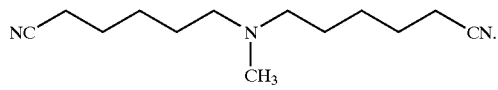

VIII

18. A method according to claim 1 wherein the resulting tertiary amine is a dinitrile, said method further comprising hydrogenating said dinitrile.

* * * * *